United States Patent [19]

Goff et al.

[11] Patent Number: 5,202,259
[45] Date of Patent: Apr. 13, 1993

[54] EXPRESSION OF HUMAN IMMUNODEFICIENCY VIRUS (HIV) REVERSE TRANSCRIPTASE

[75] Inventors: Stephen P. Goff, Tenafly, N.J.; Naoko Tanese, Berkeley, Calif.

[73] Assignee: The Trustees of Columbia University in the City of New York, New York, N.Y.

[21] Appl. No.: 291,125

[22] Filed: Dec. 28, 1988

Related U.S. Application Data

[63] Continuation-in-part of Ser. No. 865,156, May 20, 1986, abandoned.

[51] Int. Cl.$^5$ .......................... C12N 1/21; C12N 9/12; C12N 15/10
[52] U.S. Cl. ............................ 435/252.33; 435/69.1; 435/194; 435/236; 435/320.1; 935/29; 935/38; 935/73
[58] Field of Search ............. 435/320.1, 172.3, 252.33, 435/69.1, 194

[56] References Cited

U.S. PATENT DOCUMENTS

| | | | |
|---|---|---|---|
| 4,387,162 | 6/1983 | Aigle et al. | 435/172.3 |
| 4,487,835 | 12/1984 | Uhlin et al. | 435/172.3 X |
| 4,663,290 | 5/1987 | Weis et al. | 435/172.3 X |

FOREIGN PATENT DOCUMENTS

WO84/00380 2/1984 PCT Int'l Appl.

OTHER PUBLICATIONS

Barr, P. J., et al., Bio/Technology, vol. 5, pp. 486–489 (1987).
Chandra, P., et al., Cancer-Research, vol. 45, pp. 4677s–4684s (1985).
Chang, N. T., et al., Science, vol. 228, pp. 93–96 (1985).
de Clercq, E. D., Cancer Letters, vol. 8, pp. 9–22 (1979).
di Marzo Veronese, F., et al., Science, vol. 231, pp. 1289–1291 (1986).
Farmerie, W. G., et al., Science, vol. 236, pp. 305–308 (1987).
Goff, S., et al., J. Virology, vol. 38, pp. 239–248 (1981).
Hansen, J., et al., J. Biol. Chem., vol. 262, pp. 12393–12396 (1987).
Hizi, A., et al., Proc. Natl. Acad. Sci. USA, vol. 85, pp. 1218–1222 (1988).
Hoffman, A. D., et al., Virology, vol. 147, pp. 326–335 (1985).
Johnson, M. S., et al., Proc. Natl. Acad. Sci. USA, vol. 83, pp. 7648–7652 (1986).
Larder, B., et al., EMBO Journal, vol. 6, pp. 3133–3137 (1987).
Larder, B. A., et al., Nature, vol. 327, pp. 716–717 (1987).
Lightfoote, M. M., et al., J. Virology, vol. 60, pp. 771–775 (1986).
Mitsuya, H., et al., Science, vol. 226, pp. 172–174 (1984).
Muesing, M. A., et al., Nature, vol. 313, pp. 450–458 (1985).
Ratner, L., et al., Nature, vol. 313, pp. 277–284 (1985).
Rey, M. A., et al., Biochem. and Biophysical Research Communications, vol. 121, pp. 126–133 (1984).
Roth, M. J., et al., J. Biol. Chem., vol. 260, pp. 9326–9335 (1985).
Spindler, K. R., et al., J. Virology, vol. 49, pp. 132–141 (1984).
Tacon, W., et al., Molec. gen. Genet., vol. 177, pp. 427–438 (1980).
Tanese, N., et al., Proc. Natl. Acad. Sci. U.S.A., vol. 82, pp. 4944–4948 (1985).
Tanese, N., et al., J. Virology, vol. 59, pp. 743–745 (1986).
Tanese, N. and Goff, S. P., Proc. Natl. Acad. Sci. USA, vol. 85, pp. 1777–1781 (1988).
Tanese, N., et al., DNA, vol. 7, pp. 407–416 (1988).
Wain-Hobson, S., et al., Cell, vol. 40, pp. 9–17 (1985).

*Primary Examiner*—Richard A. Schwartz
*Assistant Examiner*—Johnny F. Railey, II
*Attorney, Agent, or Firm*—John P. White

[57] ABSTRACT

This invention provides a plasmid identified as pHRTRX2 and deposited in *E. coli* HB101 under ATCC Accession No. 67828. The invention also provides for a polypeptide having HIV reverse transcriptase activity and for a method by which the polypeptide can be prepared which comprises growing a host cell comprising the plasmid pHRTRX2 under suitable conditions permitting production of the polypeptide and recovering the resulting polypeptide.

3 Claims, 8 Drawing Sheets

EXPRESSION OF HUMAN IMMUNODEFICIENCY VIRUS (HIV) REVERSE TRANSCRIPTASE

This invention was made with government support under Grant Number CA 30488 from the National Cancer Institute, and Public Health Service Grant Number UO1-AI24845 from the National Institute of Health, both of the United States Department of Health and Human Services, as well as Grant Number 421 from the American Foundation for AIDS Research. The U.S. Government has certain rights in this invention.

This application is a continuation-in-part of U.S. Ser. No. 865,156, filed May 20, 1986, now abandoned, the contents of which are hereby incorporated by reference into this application.

BACKGROUND OF THE INVENTION

Within this application several publications are referenced by arabic numbers within parentheses. Full citations for these publications may be found at the end of the specification immediately preceding the claims. The disclosures of these publications in their entireties are hereby incorporated by reference into this application in order to more fully describe the state of the art to which the invention pertains.

The plasmids pHRT25 and pHRTRX2 were deposited on Oct. 25, 1988 pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 67117 and 67828, respectively.

Acquired Immune Deficiency Syndrome (AIDS) is an epidemic characterized by a marked depletion of the cellular immune response. The causative agent of the disease is now firmly established to be the human retrovirus known as Human Immunodeficiency virus (HIV), which has various forms (1-4,32,33). Efforts to arrest the spread of this virus are being made on two broad fronts: the development of antiviral vaccines which might allow immunized individuals to resist infection, and the development of antiviral drugs which would specifically retard or arrest viral replication. There have been many efforts to identify antiviral drugs with inhibitory activity against viral enzymes. One prominent target of such drugs is the virion-associated enzyme reverse transcriptase (5-8), required for the synthesis of the proviral DNA soon after infection (10,34,35). Indeed, the major antiviral drug currently prescribed, 3'-azido-3'-deoxythymidine (AZT), acts, after conversion to the corresponding triphosphate, as an inhibitor of the reverse transcriptase enzyme (36).

Several disclosures in the art concern the production of a polypeptide having reverse transcriptase activity by bacteria transformed with genetically engineered vectors. One disclosure involves the shotgun cloning into *Escherichia coli* of total genomic DNA isolated from the cells of warm-blooded vertebrate animals, e.g. fowl liver cells [Japanese patent publication no. 56087600].

Two other disclosures detail the expression of a segment of the retrovirus pol gene to produce reverse transcriptase in *E. coli* in high yield (15,16).

Co-pending, co-assigned U.S. patent application Ser. No. 731,128, filed May 6, 1985 describes the expression of enzymatically active reverse transcriptase from Moloney murine leukemia virus (MuLV) in relatively high yield.

Co-pending, co-assigned U.S. patent application Ser. No. 149,703, filed Jan. 29, 1988 describes the expression of polypeptides having DNA polymerase activity and substantially no ribonuclease activity. Much of the disclosure of U.S. application Ser. No. 149,703 has been published (31).

The expression of HIV reverse transcriptase in bacterial systems (26,27,28,29) and in yeast (30) has been reported.

The subject application is a continuation-in-part of co-pending, co-assigned U.S. patent application Ser. No. 865,156, filed May 20, 1986. Much of the disclosure of U.S. application Ser. No. 865,156 has been published (20). In U.S. Ser. No. 865,156, applicants described the expression of polypeptides having reverse transcriptase activity. Applicants' present invention provides for a series of plasmids derived from the parent construct (disclosed in U.S. Serial No. 865,156) by removal of unnecessary portions of the pol gene. These plasmids unexpectedly result in the formation of proteins with increased stability and activity.

SUMMARY OF THE INVENTION

The invention concerns a plasmid identified as pHRTRX2 and deposited in *E. coli* HB101 under ATCC Accession No. 67828.

Also provided is a method for producing a polypeptide having HIV reverse transcriptase activity which comprises growing a host cell which comprises the plasmid pHRTRX2 under suitable conditions permitting production of the polypeptide and recovering the resulting polypeptide.

The invention further provides a polypeptide having reverse transcriptase activity characterized by being encoded by the plasmid pHRTRX2.

A 3.7 kb fragment of cloned proviral HIV DNA was excised by cleavage with Bgl II plus Sal I and inserted into the expression plasmid at the BamHI and Sal I sites. Cloning procedures were as described previously (15-17). Parallel constructions were performed to insert the same pol sequences into the pATH3 vector in the wrong reading frame to form the plasmids pHRT31 and pHRT32.

Figure 2:
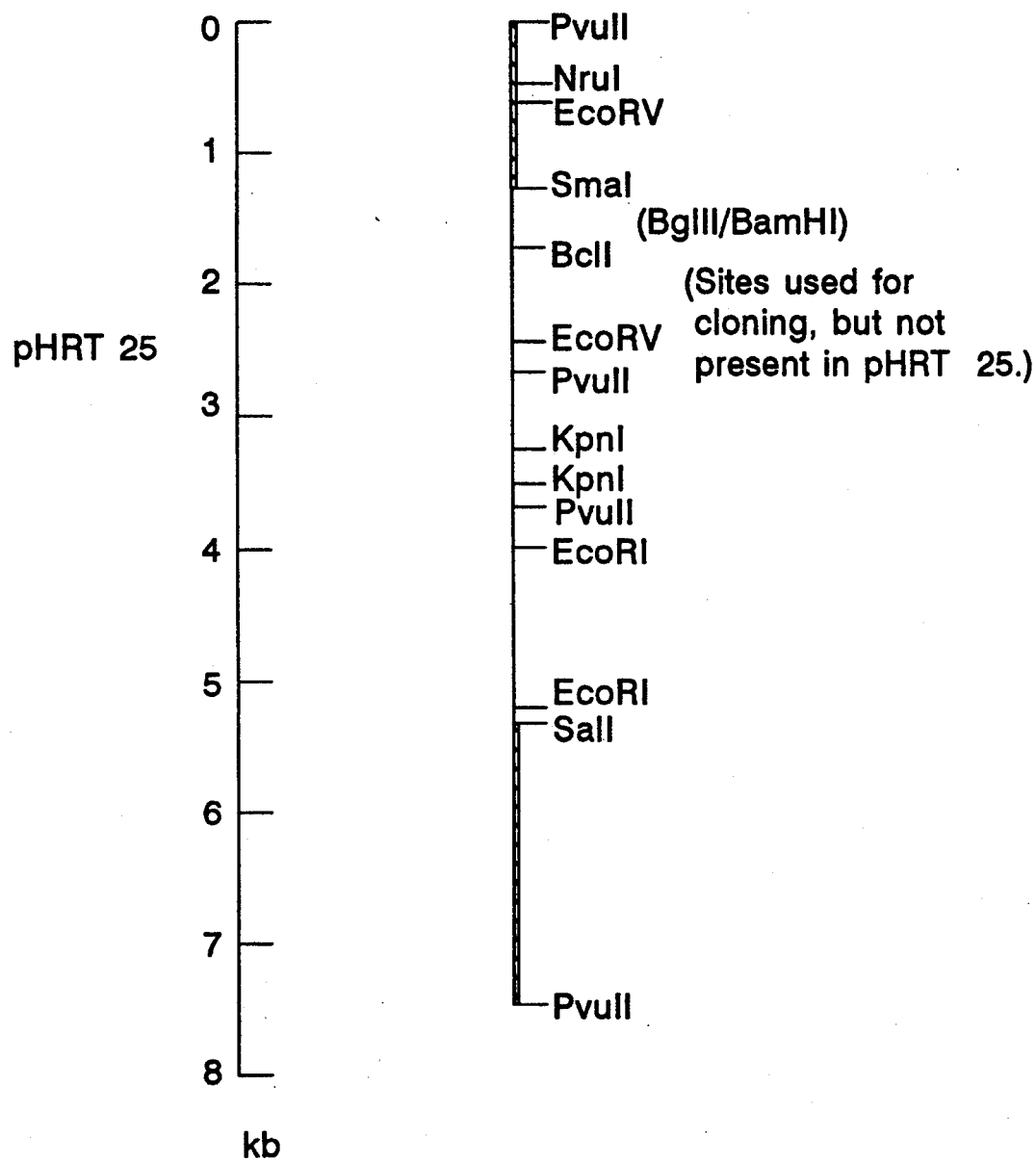

FIG. 2. Restriction map of clone pHRT25 containing pol region of HIV.

This map shows restriction sites in the vector (pATH2, dark lines) and in the insert (pol region of HIV, light lines). Start of insert is at about nucleotide 1640 (BglII site of HIV) and end of insert is at about nucleotide 5368 (SalI site in HIV) from HIV map of Ratner, et al. (12).

Figure 3A:
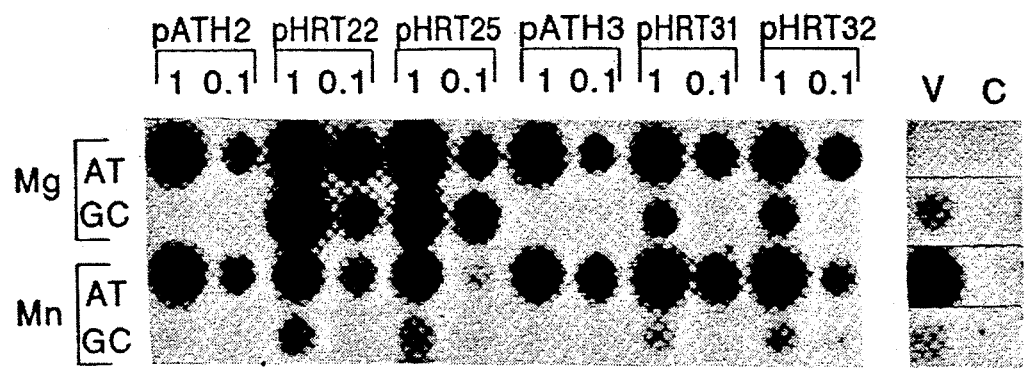

FIG. 3 Panels A and B. Reverse transcriptase assays of crude bacteria extracts.

Cultures were grown, starved for tryptophan, and lysed as described previously (13-16). Panel A: HB101 cells carrying the indicated plasmids were used. Either 1 ul or 0.1 ul of each extract as indicated was incubated in 50 ul reaction cocktails containing 50 mM Tris-HCl pH 8.3, 30 mM DTT, 60 mM NaCl, 0.05% NP40, and 10 uM of the appropriate alpha-$^{32}$P deoxyribonucleotide (1 Ci/mmole). Reactions contained either Mg$^{++}$ (10 mM) or Mn$^{++}$ (1 mM) as indicated at the left. Rows marked AT included substrates poly(rA) (10 ug/ml) and oligo(dT) (5 ug/ml), while rows marked GC included substrates poly(rC) (10 ug/ml) and oligo(dG) (5 ug/ml; all homopolymers from Collaborative Research). Reactions were allowed to proceed for 30 min, and terminated by spotting 10 ul on DEAE paper (DE81; Whatman). The paper was washed at room temperature in 2× SSC (0.3 M NaCl, 0.03 M Sodium Citrate) for 3×10 min each, rinsed twice with 95% Ethanol, dried, and exposed to X-ray film. Samples marked V and C are assays of authentic reverse transcriptase from Moloney murine leukemia virus, and of medium from control cells. Panel B: HB101 (PolA+) and C2110 (PolA1−) cells carrying the indicated plasmids were used. Assays and substrates were as in Panel A.

Figure 4:
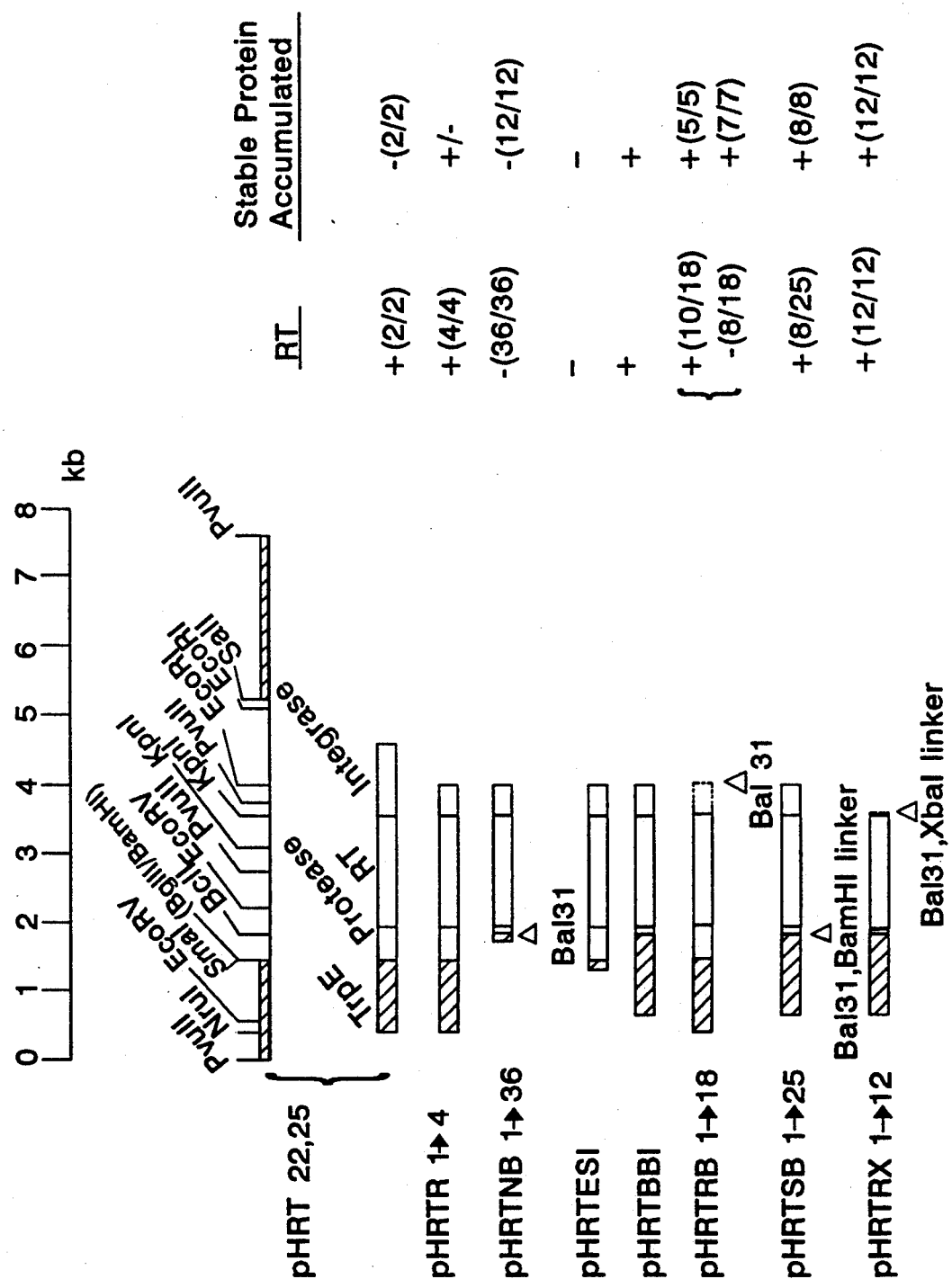

FIG. 4. Structure, stability and activity of fusion proteins encoded by various plasmids.

The complete structure and restriction map of the parental plasmids pHRT22 and pHRT25 are indicated at the top. The bold line represents vector sequences derived from pATH2 (13) and the thin line represents HIV pol gene sequences derived from pHXBc2 (12). Each box below the line represents the fusion protein encoded by the indicated plasmid construct or group of constructs. The trpE portion of each fusion protein is shaded. Open triangles denote the position of deletions of variable size generated in a group of plasmids by Ba131 digestion; oligonucleotide linkers were inserted at the sites of deletions as indicated. The properties of the fusion proteins are indicated at the right. RT: reverse transcriptase activity as detected by the standard solution assay. Stable protein accumulated: Crude cell lysates were applied to SDS polyacrylamide gels and the presence of a novel induced protein was assessed by Coomassie Blue staining. When more than one construct was scored, the number of constructs testing as indicated, out of the total number assayed, is shown in parentheses.

Figure 5A:
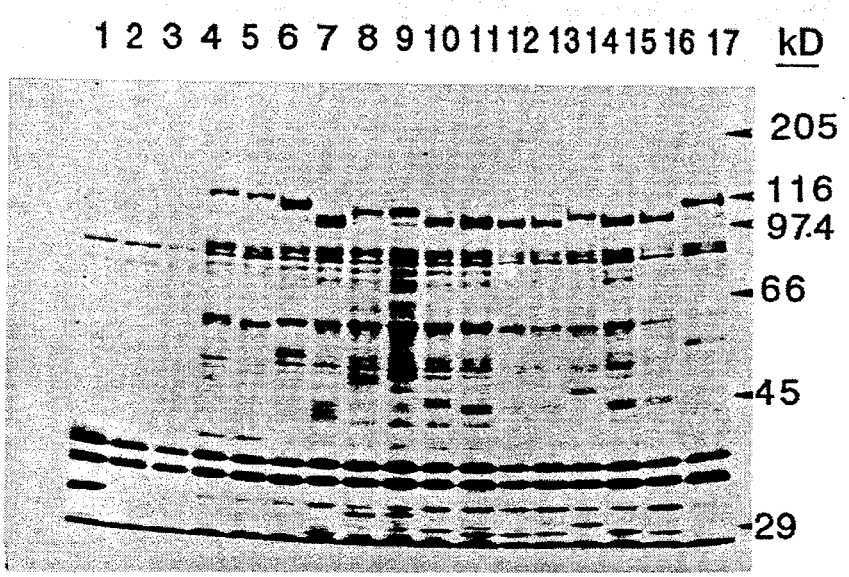
Figure 5B:
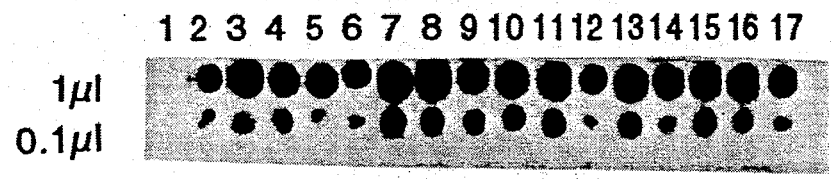

FIG. 5 Panels A and B. Analysis of extracts from bacterial clones carrying plasmids generated in the final step in the development of optimized expression plasmids.

Panel A: SDS polyacrylamide gel electrophoresis of proteins from the detergent-insoluble fraction, detected by Coomassie Blue staining. Position of migration of molecular weight standards (in kD) are indicated at the right. Panel B: Reverse transcriptase assay of extracts of the same clones of Panel A. The indicated volumes of lysate were assayed in standard 50 ul cocktails for 30 min at 37° C., spotted to DEAE paper, washed, and exposed to film. Lanes: 1, pATH2 control; 2, pHRT22 parent; 3, pHRTR3; 4, pHRTSB17; 5, pHRTSB24; 6, pHRTRX1; 7, pHRTRX2; 8, pHRTRX3; 9, pHRTRX4; 10, pHRTRX5; 11, pHRTRX6; 12, pHRTRX7; 13, pHRTRX8; 14, pHRTRX9; 15, pHRTRX10; 16, pHRTRX11; 17, pHRTRX12.

Figure 6:
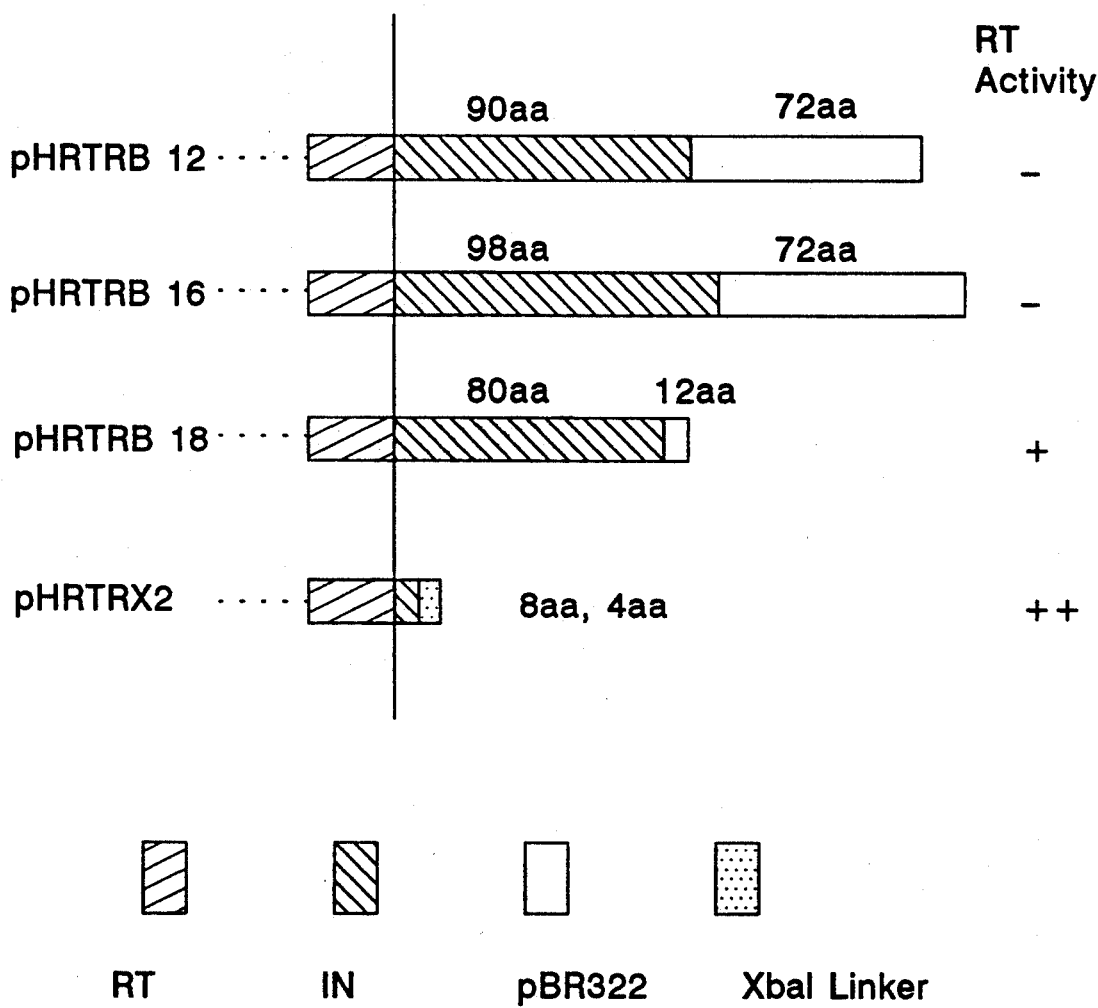

FIG. 6. Structure of the C-termini of proteins encoded by various plasmid constructs.

The nucleotide sequence of the 3′ terminal region of four expression plasmids was determined and used to predict the amino acids encoded at the C-terminus of the fusion proteins. The vertical line indicates the cleavage site separating the reverse transcriptase from integrase domains; the number of extra C-terminal residues in each construct is indicated. The origin of the residues is indicated by the coded boxes. The enzymatic activity of each protein is indicated on the right.

Figure 7A:
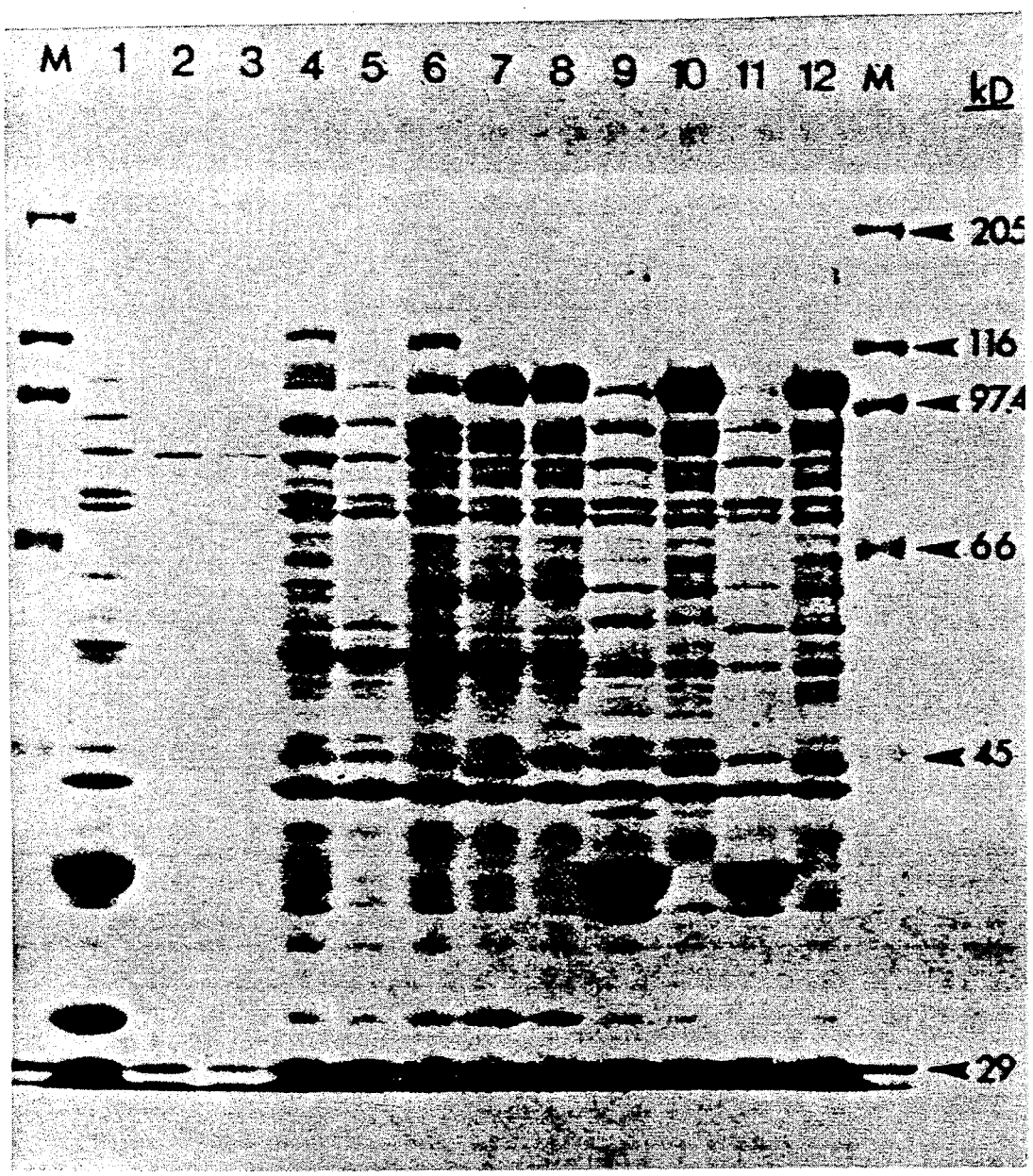

FIG. 7 Panels A, B and C. In situ reverse transcriptase assay of extracts from bacterial strains carrying various plasmid constructs.

Duplicate samples were applied to SDS polyacrylamide gels and either stained with Coomassie blue (Panel A) or electroblotted to nitrocellulose, allowed to renature, incubated in enzyme reaction cocktail, and exposed to film as described in Materials and Methods (Panel B). Results of the standard solution assay for reverse transcriptase of the same lysates are shown in Panel C. Lanes: 1, pATH2 control (in HB101); 2, pHRT25 parent (HB101); 3, pHRTR3 (HB101); 4, pHRTBB1 (HB101); 5, pHRTES1 (HB101); 6, pHRTSB17 (HB101); 7, pHRTRX2 (HB101); 8, pHRTRX6 (HB101); 9, pATH2 (B57125); 10, pHRTRX2 (B57125); 11, pATH2 (E103S); 12, pHRTRX2 (E103S). Position of migration of molecular weight standards (in kD) are indicated.

DETAILED DESCRIPTION OF THE INVENTION

A double-stranded DNA plasmid has been made which, when expressed in a suitable host cell, produces a polypeptide having HIV reverse transcriptase activity. The plasmid includes in 5′ to 3′ order: a DNA sequence which includes an inducible promoter; a DNA sequence which includes an ATG initiation codon; a portion of the Human Immunodeficiency virus (HIV) pol gene, said portion including a DNA sequence which encodes the polypeptide having HIV reverse transcriptase activity; a DNA sequence which contains a gene associated with a selectable or identifiable phenotypic trait such as drug resistance, e.g. ampicillin resistance, which is manifested when the vector is present in the host cell; a DNA sequence which contains an origin of replication from a bacterial plasmid capable of autonomous replication in the host cell, e.g., *Escherichia coli*. In one embodiment the inducible promoter of the plasmid is one which is induced when the host cell is grown upon a medium deficient in one or more amino acids. Thus, the inducible promoter may be the Trp promoter of *Escherichia coli* and the medium deficient in the amino acid tryptophan. In another embodiment the inducible promoter is one which is induced when the host cell is subjected to increased temperature.

The ATG initiation codon of the plasmid may be derived from the coding sequence of the Trp E protein of *Escherichia coli*, e.g. a DNA sequence derived from about a 1000 nucleotide long sequence encoding a portion of the Trp E protein of *Escherichia coli*. In one embodiment the origin of replication is derived from pBR322.

The plasmid may comprise a circular double-stranded DNA sequence such as the plasmid identified as pHRT25, having the restriction map shown in FIG. 2 and deposited in *E. coli* HB101 under ATCC No. 67117.

The portion of the HIV pol gene of the plasmid may comprise the nucleotide sequence from about nucleotide 1640 to about nucleotide 5368. In one embodiment the 5′ end of the central portion of the pol gene is 21 nucleotides from the start of the DNA sequence which encodes the polypeptide having reverse transcriptase activity.

The plasmid may comprise a double-stranded DNA plasmid wherein substantially all of the sequence of the pol gene which encodes the polypeptide having protease and/or integrase activity is removed, such as the plasmid identified as pHRTRX2, deposited in *E. coli* under ATCC No. 67828. In pHRTRX2 all but about 30 bp of the sequence of the pol gene which encodes the polypeptide having protease activity and all but 20 bp of the sequence of the pol gene which encodes the polypeptide having integrase activity are removed.

Methods used in preparing the DNA vector and transforming suitable cells to the production of the polypeptide having reverse transcriptase activity are known in the art and described more fully hereinafter under Experimental Details.

Conventional cloning vehicles such as plasmids, e.g., pBR322, can be modified or engineered using known methods so as to produce novel cloning vehicles which contain DNA encoding a non-naturally occurring polypeptide having reverse transcriptase activity. Similarly, such cloning vehicles can be modified or engineered so that they contain DNA sequences, i.e., inducible promoters (Trp promoter, etc.), involved in the regulation or expression of the sequences encoding a polypeptide having reverse transcriptase activity. The DNA molecules so inserted may be made by various methods including enzymatic or chemical synthesis.

The resulting cloning vehicles are chemical entities which do not occur in nature and may only be created by the modern technology commonly described as recombinant DNA technology. These cloning vehicles, including the plasmids of this invention, may be introduced into suitable host cells, either procaryotic, e.g., bacterial (*E. coli* or *B. subtilis*, etc.) or eucaryotic, e.g., yeast, using techniques known to those skilled in the art, such as transformation, transfection and the like. One embodiment of this invention is the *E. coli* HB101 strain containing the plasmid pHRT25 deposited under ATCC No. 67117. Another embodiment of this invention is the *E. coli* HB101 strain containing the plasmid pHRTRX2 deposited under ATCC No. 67828. The cells into which the plasmid of this invention is introduced will thus contain DNA encoding a non-naturally occurring polypeptide having reverse transcriptase activity. Further, the expression of the DNA encoding the non-naturally occurring polypeptide will be under the control of the Trp promoter.

The resulting cells into which DNA encoding the non-naturally occurring polypeptide encoding reverse transcriptase activity and encoding the Trp promoter has been introduced may be grown under suitable conditions known to those skilled in the art so as to control and effect the expression of the genetic information encoded by the DNA and permitting the production of the polypeptide having reverse transcriptase activity and the recovery of the resulting polypeptide. Thus one embodiment of this invention concerns the polypeptide so prepared, e.g. the polypeptide having reverse transcriptase activity characterized by being encoded by the plasmid pHRT25 or the plasmid pHRTRX2.

Another embodiment of this invention is a method for identifying substances which inhibit HIV reverse transcriptase. The method comprises isolating HIV reverse transcriptase, contacting the reverse transcriptase so isolated with an RNA molecule to be reverse transcribed in the presence of a suitable amount of a mixture of deoxyribonucleotides to produce a transcription cocktail, contacting the transcription cocktail with an amount of a substance to be identified for a suitable period and detecting the amount of reverse transcriptase activity in the cocktail, a significant decrease in the amount of reverse transcriptase activity relative to the amount of activity in a cocktail not contacted with the substance indicating an inhibition of the reverse transcriptase activity.

In the preferred embodiment, HIV reverse transcriptase will be isolated from cells, i.e. bacterial or yeast cells containing plasmids comprising the HIV pol gene, i.e. plasmid pHRT22 or pHRT25 or PHRTRX2. HIV reverse transcriptase may also be isolated from other sources, i.e., tissue culture cells infected with the HIV virus. Methods used in isolating HIV reverse transcriptase are known in the art and are described more fully hereinafter under Experimental Details.

Mixtures of deoxyribonucleotides to be used in the present invention will contain dATP, dGTP, dCTP and dTTP in relative amounts suitable to each experiment.

In the preferred embodiment, detecting the amount of reverse transcriptase activity comprises detecting by autoradiography the amount of one or more radiolabelled deoxyribonucleotides, i.e. $^{32}$P-ATP, incorporated by the reverse transcriptase. Other methods, i.e., quantitative immunoassay, may also be useful.

Still another embodiment of this invention is a method for treating an HIV virus-related disease in a subject. The method comprises administering to the patient a suitable amount of a physiologically acceptable HIV reverse transcriptase inhibiting substance for a suitable period.

The substance may be administered by a variety of methods, including injection in a pharmaceutically acceptable carrier, i.e. intravenously or peritoneally, topical application, oral application in a liquid or solid form or a variety of other routes well known in the art.

MATERIALS AND METHODS

Bacteria and plasmids. *E. coli* strain HB101 was used as the host for all experiments unless indicated. Strain GM33 (dam-3; Dr. Marinus, Rutgers University) was used as host to prepare DNAs for cleavage by BclI. Strains B57125 (*E. coli* B, L. Simon, Waksman Institute, Rutgers University) and E103S (*E. coli* K12 met−), were generous gifts form M. Knapp (Columbia University). All bacterial transformations were by standard procedures (19). Parental plasmids pHRT22 and pHRT25 are described below.

Enzymatic manipulation of plasmids DNA. Digestions of DNA with restriction enzymes and exonuclease Ba131 (New England Biolabs) were by standard procedures (22). Linkers containing either the BamHI recognition site (12 bp; N.E. Biolabs #1015) or the XbaI site (N.E. Biolabs #1062) were inserted at sites of some cleavages. DNA framents were purified by agarose gel electrophoresis and recovered by the glass powder method (22). Linear DNAs were circularized by treatment with T4 DNA ligase at low DNA concentrations (1-10 ug/ml).

CONSTRUCTION OF PLASMIDS

Figure 1:
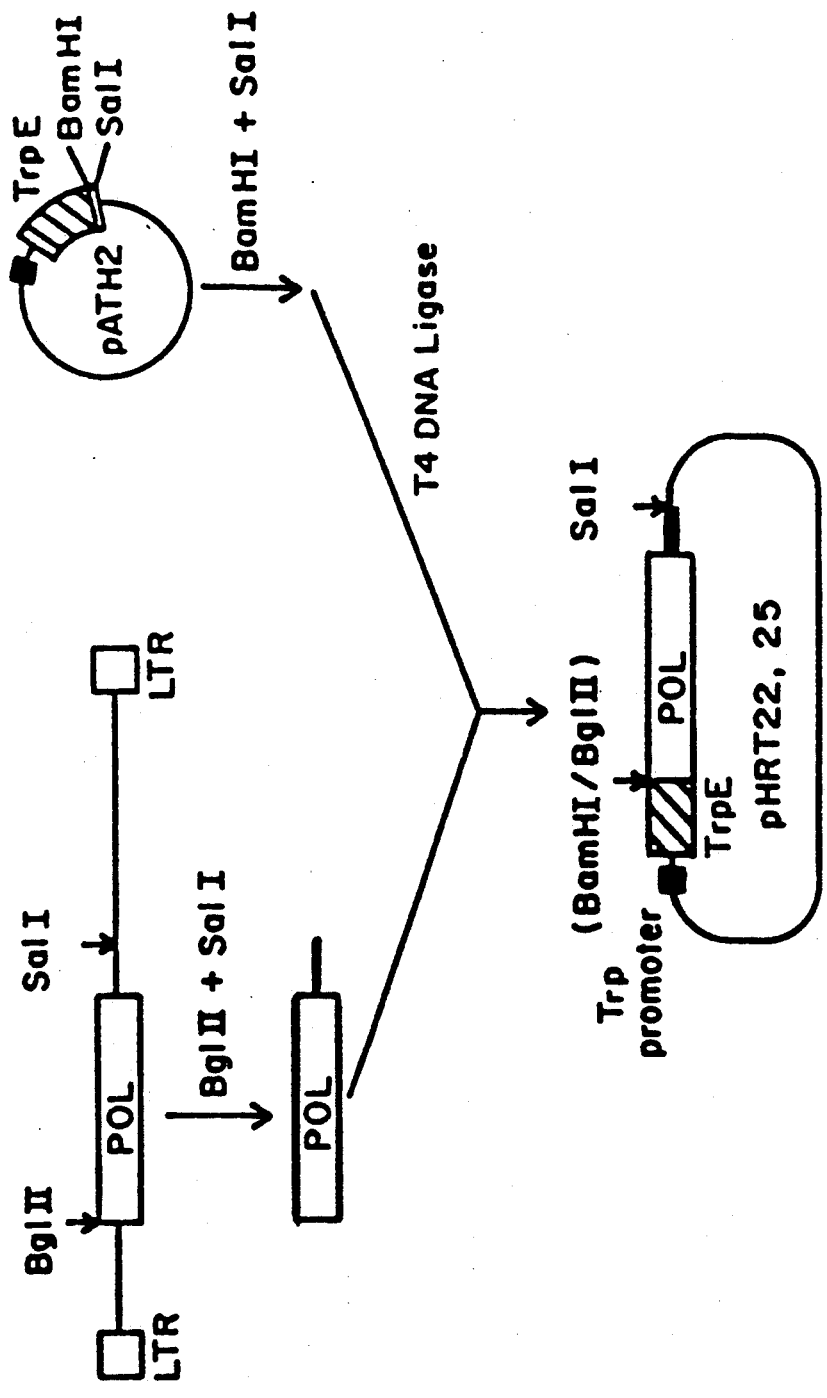
FIG. 1. Construction of active gene fusion.

To facilitate the preparation of the HIV enzyme, gene fusions have been prepared between the trpE gene of *E. coli* and the appropriate portion of the viral pol gene. A large DNA fragment that contains almost all of the pol gene was excised from a biologically active proviral clone (pHXBc2; (12)) and inserted into the pATH2 expression vector by fusion of the 5' half of the trpE gene to the pol sequences in the correct reading frame (FIG. 1). Two duplicate clones of the resulting plasmids, pHRT22 and pHRT25, were selected for analysis. A detailed restriction map of one of the clones, pHRT25, is shown in FIG. 2. Clones pHRT22 and pHRT25 have essentially similar restriction maps. Parallel constructions were performed to insert the same pol sequences into the pATH3 vector in the wrong reading frame to form the control plasmids pHRT31 and pHRT32.

pHRTR1-4 were made by digestion of the parent pHRT22 with EcoRI and circularization, to remove the 1.1-kb region at the 3, part of the HIV pol gene. pHRTNB1-36 were made by cleavage of pHRTR3 with BclI, digestion with Bal31 to remove an average of approximately 100 bp from each end, digestion with NruI, and circularization. pHRTES1 was made by digestion of pHRTR3 to completion with SmaI and partially with EcoRV, and circularization. pHRTBB1 was made by digestion of pHRTR3 with BclI plus SalI, and transfer of the resulting 2.3 kb fragment into the pATH2 vector (13) after its digestion with BamHI plus SalI. pHRTRB1-18 were made by cleavage of pHRTR3 with EcoRI, digestion with Bal31 to remove about 300 bp from each end, and circularization. pHRTSB1-25 were made by cleavage of pHRTR3 with BclI, digestion with Bal31 to remove about 100 bp from each end, cleavage with SmaI, addition of BamHI linkers, digestion with BamHI, and circularization. pHRTRX1-6 were made by cleavage of pHRTSB17 with EcoRI, digestion with Bal31 to remove about 300 bp from each end, addition of XbaI linkers, cleavage with XbaI, and circularization. pHRTRX7-12 were similarly derived from pHRTSB24.

Plasmids pHRT22 and pHRT25

Bacterial cultures containing various plasmids were grown in minimal medium, starved for tryptophan, and exposed to indoleacrylic acid to derepress the trp operon (13-16). After 2 h, the cells were harvested, lysates were prepared, and the crude extracts were assayed directly for reverse transcriptase activity (FIG. 3A) as described previously (15-17). The extracts were tested for their ability to incorporate the appropriate radioactive triphosphate on either of two substrates: poly(rA) primed with oligo(dT), or poly(rC) primed with oligo (dG). Each substrate was tested with either of two divalent cations: $Mg^{++}$ (10 mM), or $Mn^{++}$ (1 mM).

All the cultures, no matter what plasmids they carried, showed considerable background activity on the poly(rA): oligo(dT) substrate; only a slightly higher level of activity was apparent from cells carrying the pHRT22 and pHRT25 constructs. In contrast, assays on the poly(rC): oligo(dG) substrate gave a dramatic result. Cells carrying the vector DNA showed essentially no background activity, while cells containing pHRT22 and pHRT25 yielded high levels of activity (FIG. 3, panel A, row 2). The activity was highly specific for $Mg^{++}$ as the divalent cation (compare rows 2, 4). This behavior was distinct from the activity of the murine reverse transcriptase, which is most active on the poly(A): oligo(dT) template with $Mn^{++}$ (column V). Control plasmids formed with fusions out of frame showed a trace of activity, only slightly above background.

Figure 3B:
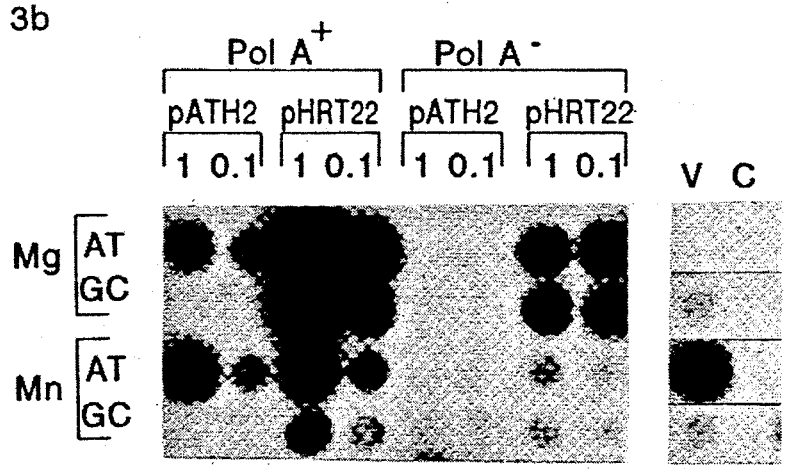

In an attempt to reduce the background of DNA polymerase activity on the poly(rA): oligo(dT) template, the plasmids were transferred into a bacterial strain deficient in DNA Polymerase I (17). These cells do not support replication of the plasmid DNA, and transformants carry the plasmid DNA integrated into the host chromosome only in one or a few copies. Extracts were prepared and assayed as before (FIG. 3B).

PolyA$^-$ cells carrying the vector plasmid pATH2 showed no detectable background activity on either template, with either divalent cation. These same cells carrying the pHRT22 construct showed high levels of activity in the presence of $Mg^{++}$; activity could be detected on either poly(rC): oligo(dG) or on poly(rA): oligo(dT), but there was slightly higher activity on the poly(rC) oligo(dG) template. There was very little activity in the presence of $Mn^{++}$ on either template. These properties of the activity duplicate precisely the behavior of the authentic HIV reverse transcriptase enzyme as purified from virion particles (9-11).

To obtain a quantitative measure of the level of activity, assays were repeated on poly(rC): oligo(dG) template with $Mg^{++}$, and the amount of incorporated radioactivity was determined by scintillation counting. Assays lacking either primer or template showed only background activity (data not shown). Titration of the extracts in reactions allowed to proceed for 10 min showed that the assay was linear with up to 1 ul of extract (Table 1).

TABLE 1

| | Titration of Extracts | | |
|---|---|---|---|
| Cell line | Volume of Extract (ul) | dGTP incorporated pmol/10 min | specific activity (pmol/10 min/ug protein) |
| HB101(pATH2) | 0 | 0 | |
| | 0.2 | 0.035 | |
| | 0.06 | 0.035 | |
| | 0.1 | 0.035 | 0.02 |
| | 0.3 | 0.035 | |
| | 1.0 | 0.035 | |
| HB101(pHRT22) | 0 | 0 | |
| | 0.02 | 0.6 | |
| | 0.06 | 0.8 | |
| | 0.1 | 1.9 | 4.3 + 0.07 |
| | 0.3 | 4.2 | |
| | 1.2 | 14.1 | |

Legend
Extracts from the indicated cultures were prepared as before (15-16). The indicated volumes of the extracts were incubated in reaction mixes (50 ul total volume) containing 50 mM Tris-HCl pH 8.3, 20 mM DTT, 60 mM NaCl, 0.05% NP40, 10 mM $MgCl_2$, 10 ug/ml poly (rC), 5 ug/ml oligo(dG), and 10 uM $a^{-32}P$-dGTP (1 Ci/mmole).

Reactions were carried out for 10 min at 37° C. The reaction mix was spotted on squares of DEAE paper, the papers were batch-washed in 2× SSC, rinsed in ethanol and dried, and the incorporated counts were measured by scintillation counting. Background counts of 220 CPM present in reactions without extracts were subtracted before calculation of the pmoles of nucleotide incorporated. Protein determinations, performed by the method of Bradford (18), gave concentrations for HB101(pATH2): 4.4 mg/ml; and HB101(pHRT22): 3.3 mg/ml. The specific activity of the extracts was calculated from the slope of a least squares fit of the titration data.

Extracts of cells carrying the pHRT22 constructs showed more than a 200-fold increase in specific activity over extracts from control cells. Analysis of the time course of the reaction, using 0.1 ul of extract, showed that the reaction was linear for more than 10 minutes (Table 2). These experiments also showed large increases in the specific activity of cells carrying the pHRT22 constructs relative to controls. The PolA$^-$ cells with pHRT22 yielded about 5-fold less activity that the PolA+ cells carrying the same plasmid, presumably due to the lower copy number of the plasmids in the PolA⁻ cells.

TABLE 2

Time Course of Incorporation

| Cell in | Time (min) | dGTP incorporated (pmol/ug protein) | specific (pmol/ug protein/10 min) |
|---|---|---|---|
| HB101(pATH2) | 0 | 0 | |
| | 1 | 0.1 | |
| | 5 | 0.1 | |
| | 10 | 0.1 | 0.05 |
| | 20 | 0.1 | |
| | 40 | 0.1 | |
| HB101 (pHRT22) | 0 | 0 | |
| | 1 | 0.4 | |
| | 2 | 0.4 | |
| | 5 | 1.1 | 1.7 + 0.1 |
| | 10 | 2.1 | |
| | 20 | 3.5 | |
| | 40 | 6.5 | |
| C2110(pATH2) | 0 | 0 | |
| | 1 | 0.07 | |
| | 2 | 0.07 | |
| | 5 | 0.07 | 0.03 |
| | 10 | 0.07 | |
| | 20 | 0.07 | |
| | 40 | 0.07 | |
| C2110 (pHRT22) | 0 | 0 | |
| | 1 | 0.004 | |
| | 2 | 0.06 | 0.30 + 0.03 |
| | 5 | 0.2 | |
| | 10 | 0.2 | |
| | 20 | 0.6 | |
| | 40 | 1.2 | |

Legend
0.1 ul of crude extracts from the indicated cultures were incubated in reaction mixes for the indicated times, and the incorporated counts were determined as in Table 1. Background activity of 150-200 CPM were substracted before calculating activities. Protein concentrations were as follows. HB101(pATH2): 4.4 mg/ml; HB101(pHRT22): 3.3 mg/ml; C2110(pATH2): 3.9 mg/ml; C2110(pHRT22): 5.2 (mg/ml). Specific activities were determined as before.

With plasmids pHRT22 and pHRT25, the HIV pol gene has been inserted into a bacterial expression plasmid and it has been demonstrated that the construct induces reverse transcriptase activity. The appearance of activity depends on the joining of the trpE and pol sequences in the correct reading frame, and is independent of the bacterial polA gene. The resulting activity closely mimics the behavior of the authentic HIV enzyme, strongly preferring Mg++ over Mn++, and differs sharply from the enzyme encoded by the murine leukemia viruses. It is expected that these constructs and more active derivatives described below will be useful in the genetic analysis of the functions of the HIV pol gene, and in surveys for antiviral agents.

PLASMIDS PRODUCING MORE STABLE, MORE ACTIVE PROTEINS

HIV Reverse Transcriptase Assays. Growth of bacteria, induction of the trp operon, lysis with lysozyme and detergent, and preparation of the insoluble and soluble fractions were all as described above (see also 16, 20). Assays of the DNA polymerase activity of HIV reverse transcriptase measured the incorporation of alpha-$^{32}$P-dGTP (10 uM) on homopolymeric substrates (poly(rC) at 10 ug/ml and oligo(dG) at 5 ug/ml; Collaborative Research) in standard buffer conditions (50 mM Tris.HCl, pH 8.3, 60 mM NaCl, 10 mM MgCl$_2$, 20 mM DTT, 0.05% NP40), as described previously (20). Incorporated radioactivity was determined by spotting the reaction mix onto DE-81 paper, washing, and exposing the paper to X-ray film or scintillation counting (17).

In situ reverse transcriptase assay. This assay was a modified version of procedures devised for detection of the Moloney murine leukemia virus (MuLV) reverse transcriptase (15). Bacterial cultures were grown, induced, and lysed as for the standard assay, and the proteins remaining insoluble in NP40 were isolated by centrifugation. The pellet was dissolved in SDS-urea sample buffer (1% SDS, 1% β-mercaptoethanol, 0.01 M sodium phosphate, pH 7.2., 6 M urea) and applied to standard SDS polyacrylamide gels (23). After electrophoresis (200 v, 5 h at room temperature), the proteins were electroblotted onto nitrocellulose paper (Schleicher and Schuell) using standard procedures (24) in buffer (20 mM Tris base, 200 mM glycine) at room temperature. The paper was incubated for 1 h at room temperature in buffer (30 mM Hepes, pH 7.5) containing 0.02% bovine serum albumin (Fraction V, Sigma) to block nonspecific binding of nucleotides, and then further incubated in buffer (50 mM Tris.HCl, pH 7.5, 1 mM EDTA, 2 mM DTT, 0.2 M NaCl, 10% glycerol, and 0.1% NP40) overnight at 4° C. with several changes of buffer, to allow renaturation of the bound protein. The paper was placed in a heat-sealable bag and preincubated in reverse transcriptase reaction cocktail as above but without nucleotide for 30 min at room temperature. The bag was drained and refilled with complete reaction cocktail (1-2 ml for a typical 10×10 cm sheet) including radiolabeled alpha-$^{32}$P-dGTP (10 uM; 1 Ci/mmole) and incubation was continued for 1 h at room temperature. At the end of the reaction the paper was washed and fixed in 10% TCA for 10 min at room temperature with one change of the solution. Finally the paper was air-dried and exposed to X-ray film.

DNA sequence analysis. The nucleotide sequence of the 3'-terminal region of selected clones was determined by the Maxam-Gilbert procedure. Plasmid DNAs were cleaved with Ava I, and the 3' ends in the HIV pol gene were selectively labeled with DNA polymerase and alpha-p$^{32}$dCTP. After purification the relevant fragment was subjected to analysis by standard methods (25).

RESULTS

Overview: construction and analysis of new gene fusions expressing HIV reverse transcriptase activity The parent plasmid for all the constructions, pHRT22, contained a portion of the trpE gene fused to the entire open reading frame of the pol gene of HIV-1 (FIG. 4) (20). Thus, the pol portion of this construct contained the coding region for all three of the pol domains: the protease, reverse transcriptase, and integrase functions, as predicted by the nucleotide sequence of the viral genome (12). To generate more stable and active proteins, applicants eliminated different portions of the unwanted coding regions using a combination of restriction enzyme and Bal31 exonuclease digestions. In each series of variant plasmids, the appearance of the expected alteration in the DNA was confirmed by agarose gel electrophoresis of rapid lysis preparations of the DNA. A summary of the structures of all the novel fusion proteins encoded by the plasmids generated in this study is shown in FIG. 4.

To determine the consequences of the alterations on protein stability and enzyme activity, lysates of bacterial cultures carrying each new variant were prepared. The level of reverse transcriptase recovered in each lysate was directly measured on synthetic homopolymeric templates (poly(rC) primed with oligo(dG)), and the incorporation of labeled triphosphate precursor was scored by comparison with control lysates containing either the parental pHRT22 or the vector plasmid lacking HIV sequences. The level of accumulated protein was measured by SDS polyacrylamide gel electrophoresis of either the crude lysate or the triton-insoluble fraction, followed by Coomassie staining, and the recovery of a visible new protein of the size expected from the plasmid structure was scored after destaining. The results for each series of variants are summarized in FIG. 4.

Initial contructs: consequences of truncating the C-terminus and removing the N-terminal trpE sequence The majority of the the C-terminal integrase sequences were first eliminated by removal of an Eco RI fragment from the parent plasmid (FIG. 4). Four identical clones (pHRTR1-4) all showed substantially improved levels of enzyme activity, approximately 2-5 fold higher than the pHRT22 parent, suggesting that the deleted protein was modestly more stable or active. This deletion was retained in the starting plasmids for subsequent manipulations. No fusion protein, however, accumulated to a sufficiently high level to be detected on stained gels in most experiments (see FIG. 5A, lane 3). A faint band of the size expected for this construct, 135 kd, could rarely be detected in such gels (data not shown).

A series of constructs was next made to remove simultaneously the bulk of the trpE region and different extents of the protease region. Deletions extending from a fixed endpoint at codon 18 of trpE to variable sites in the protease were made in pHRTR3. A total of 36 independent clones (pHRTNB1-36; FIG. 4) were tested for enzyme activity to ensure that at least some deletions recreated the correct translational reading frame. Although 12 clones were expected to be in the correct frame, none yielded any detectable enzyme activity, and 12 of the 36 clones selected at random showed no stable protein accumulating in the cells. In all these clones, both the trpE and protease regions were largely deleted, and the failure of these variant constructs to yield stable proteins suggested that at least one of these domains might have been helpful in stabilizing the products of applicants' initial plasmid.

To determine whether the protease or trpE region was more important for the recovery of protein, applicants made one plasmid lacking the bulk of the trpE domain but retaining the protease region (pHRTES1), and another lacking the protease but retaining the trpE (pHRTBB1). Analysis of cultures carrying these constructs showed that retention of the trpE domain was important for the recovery of enzyme activity; retention of the protease domain was not helpful in this system. Analysis of lysates on SDS gels showed that the product encoded by pHRTBB1 was stable and accumulated to substantial levels after induction. The size of the major new protein (120 kD) was as predicted by the structure of the gene fusion, although smaller proteins were also detected.

Optimized constructs: trimming of the protease and integrase domains

The results of the analyses described above suggested that removal of at least parts of the protease and integrase domains of the HIV pol gene from the constructs could result in improved recovery of reverse transcriptase activity. To maximize that recovery, applicants successively trimmed variable portions of both domains from pHRTR3 and screened a collection of cultures carrying these derivative plasmids for enzyme activity.

A series of 18 deletions at the 3' end of the pol gene were generated by Bal31 exonuclease such that translation would proceed through the pol sequences into the plasmid vector and terminate at the first stop codon (plasmids pHRTRB1-18; FIG. 4). Significant levels of enzyme activity were detected in extracts of 10 clones, but only low levels of activity above controls were found in the remaining 8 clones. Substantial levels of stable protein were accumulated in all of 12 cultures tested. Examination of the structure of the DNAs in the two classes of clones yielded no invariant rules which could account for the two phenotypes. However, there was a tendency for those clones retaining more of the HIV pol gene to be inactive, and for those clones retaining less to be more active. These results indicated that the integrase domain could indeed be trimmed to give improved activity, but that amino acid sequences appended to the C-terminal end of the protein could have critical and variable effects.

To test whether the newly appended amino acids were important determinants of activity, the nucleotide sequence of the fusion point was determined in three selected clones, two encoding inactive proteins and one encoding an active protein. The results showed that the inactive proteins contained unusually long stretches of foreign sequence (FIG. 6). Although the fusion points in the HIV pol gene in these two clones were different, the sequences appended were identical and were translated in the same frame; presumably this reflected a tendency of the Bal31 to pause frequently at particular positions during the trimming. The fact that these C-termini were identical suggests that this sequence may be particularly deleterious to enzymatic activity. The single active protein, formed by fusion to vector sequences that were translated in a different reading frame, retained only a short stretch of foreign amino acids (FIG. 6). Applicants conclude that certain appended sequences, particularly long ones, can profoundly affect activity.

The final development of an optimized protein of minimal size involved the trimming of both protease and integrase domains, with insertion of synthetic linkers at the sites of deletions to facilitate further manipulations and to ensure immediate translational termination at the C-terminus. Deletions extending from a fixed point at the 3' end of the trpE sequences to variable points in the protease domain were generated from the parental plasmid pHRTR3, and BamHI linkers were inserted at the site of the deletion. Out of 25 clones tested (pHRTSB1-25), a total of 8, close to the expected one-third, exhibited high levels of reverse transcriptase activity; all eight contained an abundant, stable protein (see FIG. 5A, lanes 4 and 5 for examples). Two of these 8 clones (pHRTSB17 and 24) were selected for further trimming in the integrase region. Deletions were generated in this region with Bal31, and XbaI linkers containing translational termination codons in all three reading frames were inserted at the site of the deletions. Analysis of 12 such clones (pHRTRX1-12) showed that all exhibited comparable levels of reverse transcriptase activity. The uniformly high level of activity found, in contrast with the results of the pHRTRB series described above, suggests that the cleanly terminated C-terminus was significantly helpful. Examination of the proteins by SDS gel electrophoresis showed that all 12 accumulated substantial levels of new proteins in the 100–110 kD size range, and in some cases, smaller proteins, presumably proteolytic breakdown products, could also be detected (FIG. 5A, lanes 6–17). One clone, pHRTRX2, was selected as encoding a particularly stable protein species. As judged by analysis of the DNA, this clone contained all of the HIV reverse transcriptase region, and only about 30 bp of extra protease sequence and 20 bp of extra integrase sequence. Sequence analysis of the 3' terminal region showed that only 8 amino acids of the integrase region and 4 amino acids from the linker were appended beyond the authentic C-terminus of the p66 HIV RT (see FIG. 6). Thus, very little of the pol region beyond that needed to encode the p66 form of reverse transcriptase was retained at either end.

Figure 7B:
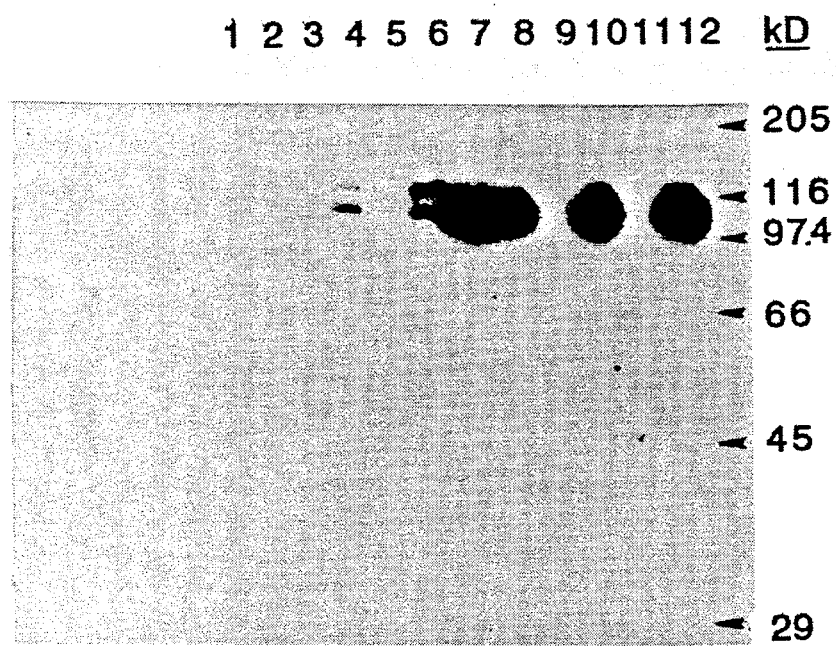

Size of active protein species: in situ polyacrylamide gel activity assay for reverse transcriptase Since extracts of many of the bacterial clones exhibited several smaller species along with the major full-sized protein, the identity of the enzymatically active proteins remained uncertain. To determine which species were active, applicants made use of an in situ activity assay capable of detecting RNA-dependent DNA polymerase activity after the separation of proteins by SDS polyacrylamide gel electrophoresis. Extracts from a collection of clones from various stages in the development of the optimized construct were prepared, and the proteins were separated by electrophoresis on duplicate conventional SDS polyacrylamide gels (23). After electrophoresis one gel was stained with Coomassie (FIG. 7A); the proteins were electroblotted from the duplicate gel onto a nitrocellulose sheet, renatured on the paper, and incubated in a standard reverse transcriptase cocktail containing synthetic homopolymer substrates and labeled triphosphates. After the reaction the paper was fixed with acid and exposed to autoradiography (FIG. 7B). The renatured proteins incorporated label into DNA, and sufficient labeled product was retained on the paper to permit detection of the active species. Controls showed that the reaction was absolutely dependent on template, as was the standard reaction.

Figure 7C:
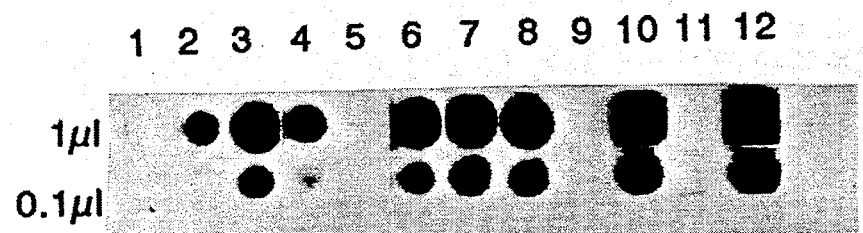

SDS gels of extracts from earlier constructs (pHRT25, pHRTR3) did not reveal any discrete bands of induced protein, as shown before (FIG. 7A, lanes 2 and 3), and the in situ assay did not reveal any species with recoverable activity (FIG. 7B, lanes 2 and 3), although enzyme activity was readily detected in the crude lysate assayed conventionally (FIG. 7C). Applicants conclude that the active proteins were too heterogeneous in size, that the level of accumulated protein was too low, or that the ability of the protein to renature after electrophoresis was too poor, to allow detection of the activity. Extracts of clone pHRTES1, lacking the trpE domain, showed no stable induced proteins, no discrete active species, and no enzyme activity by the conventional assay (FIG. 7, lane 5), as described earlier. In contrast, extracts from clones pHRTBB1 and pHRTSB17, lacking the protease domain, exhibited several induced proteins by stain, and showed a distinct doublet of active enzymes (FIG. 7B, lanes 4 and 6). The larger band corresponded to the size of the full-length product, and the smaller corresponded to one of the smaller proteins visible by stain. None of the other smaller induced proteins showed activity. Applicants conclude that for these clones, the larger proteins were able to renature and recover at least some enzyme activity, while the smaller products could not. Extracts from the optimized clones, pHRTRX2 and pHRTRX6 (FIG. 7, lanes 7 and 8) each revealed a single major induced protein of 100 kd as before, and the activity gel showed that high levels of activity were associated with these bands. No smaller proteins showed any activity. Applicants conclude that for these clones, the major stable protein carried all of the recoverable activity.

The activity of the optimized clone pHRTRX2 was not restricted to host HB101 but was readily expressed by several different strains of E. coli. Two healthy strains of E. coli commonly used for production of recombinant proteins were transformed with the plasmid, and cultures were induced as for HB101. These strains were found to grow far more rapidly and to far higher densities; even higher levels of activity were recovered from these strains, judged either by the in situ or conventional assays (FIG. 7B, C).

DISCUSSION

Although applicants' initial construct, pHRT22, induced substantial levels of reverse transcriptase activity (20), no new, stable proteins could be detected in crude lysates after induction. Applicants note that cultures expressing this and other very large fusion proteins often grow poorly; sometimes the total yield of protein obtained after lysis is lower than for control cultures (cf. lanes 2 and 3 with other lanes in FIG. 7A). Possibly the expression of these proteins is toxic to the cells. The sensitive and rapid enzymatic assay can be used to locate even trace levels of the protein that are undetectable on gels, however, and is well suited for testing modified constructs for increased activity. The trimming of the protease and integrase regions from the construct as described here made unexpected, dramatic improvements in the yield. Clearly multiple steps in the ultimate formation of active enzyme in bacteria might have been affected by the modifications: the folding and stability of RNA transcripts; their translational efficiency; and perhaps most importantly, the stability, folding and inherent activity of the fusion proteins. The protein encoded by the final construct, pHRTRX2, was stable and as judged by the in situ assay, carried all the activity detected after blotting. Further work with this protein has demonstrated that it also exhibits RNase H activity with a requirement for $Mg^{++}$ (data not shown); in all respects tested, the bacterial protein mimics the behavior of the authentic enzyme (9,11).

The mutational studies described in this application led to the finding that the retention of the trpE domain on the HIV fusion proteins significantly improved the recovery of stable protein. This behavior was distinct from the results obtained with Moloney murine leukemia virus reverse transcriptase (15,16), where the trpE domain could be removed. Applicants' attempts to remove the bulk of the trpE domain from the HIV constructs resulted in the complete loss of the protein and its activity; applicants have made similar observations with expression of the HIV integrase domain in bacteria (data not shown). Applicants conclude that the major affects of the trpE domain occur posttranslationally because all of the constructs include the same transcriptional and translational start signals. Much of the improved stability with trpE may be due to the tendency of the fusion protein to precipitate from solution. Indeed, the majority of the protein in all of applicants' constructs was recovered in the insoluble fraction of the extract (data not shown). Any protein that partitions into the insoluble fraction in this way is presumably sequestered from proteases that otherwise would degrade it. It is also possible that the trpE region directly protects the soluble fraction of the fusion protein from proteolysis.

REFERENCES

1. R. C. Gallo et al., *Science* 220, 865 (1983).
2. F. Barre-Sinoussi et al., *Science* 220, 868 (1983).
3. R. C. Gallo et al., *Science* 224, 500 (1984).
4. A. S. Fauci et al., *Ann. Intern. Med.* 100, 92 (1984).
5. P. Chandra, *Top. Curr. Chem.* 52, 99 (1974).
6. E. DeClercq, *Cancer Lett.* 8, 9 (1979).
7. J. B. McCormick et al., *Lancet II*, 1367 (1984).
8. H. Mitsuya et al., *Science* 226, 172 (1984).
9. M. A. Rey, B. Spire, D. Dormont, F. Barre-Sinoussi, L. Montagnier, and J. C. Chermann, *Biochem. Biophys. Res. Commun.* 121, 126 (1984).
10. P. Chandra, A. Vogel, and T. Gerber, *Cancer Res.* (Suppl.) 45, 4677s (1985).
11. A. D. Hoffman, B. Banapour, and J. A. Levy, *Virology* 147, 326 (1985).
12. L. Ratner et al., *Nature* 313, 277 (1985).
13. K. R. Spindler et al., *J. Virol.* 49, 132 (1984).
14. D. G. Kleid et al., *Science* 214, 1125 (1981).
15. N. Tanese, M. Roth, and S. P. Goff, *Proc. Natl. Acad. Sci. U.S.A.* 82, 4944 (1985).
16. M. J. Roth, N. Tanese, and S. P. Goff, *J. Biol. Chem.* 260, 9326 (1985).
17. S. P. Goff, P. Traktman, and D. Baltimore, *J. Virol.* 38, 239 (1981).
18. M. M. Bradford, *Anal. Biochem.* 72, 248 (1976).
19. M. Mandel and A. Higa, *J. Mol. Biol.* 53, 159 (1970).
20. N. Tanese, J. Sodroski, W. A. Haseltine, and S. P. Goff, *J. Virol.* 59, 743 (1986).
21. T. Maniatis et al., Molecular Cloning, Cold Spring Harbor Laboratory, Cold Spring Harbor, N.Y. (1982).
22. B. Vogelstein and B. Gillespie, *Proc. Natl. Acad. Sci. U.S.A.* 76, 615 (1979).
23. U. K. Laemmli, *Nature* (London) 227, 680 (1970).
24. B. Bowen et al., *Nucl. Acids Res.* 8, 1 (1980).
25. A. Maxam and W. Gilbert, *Methods Enzymol.* 65, 499 (1980).
26. W. G. Farmerie et al., *Science* 236, 305 (1987).
27. B. Larder et al., *EMBO J.* 6, 3133 (1987).
28. J. Hansen et al., *J. Biol. Chem.* 262, 12393 (1987).
29. A. Hizi et al., *Proc. Natl. Acad. Sci. U.S.A.* 85, 1218 (1988).
30. P. J. Barr et al., *Bio/Technology* 5, 486 (1987).
31. N. Tanese and S. P. Goff, *Proc. Natl. Acad. Sci. U.S.A.* 85, 1777 (1988).
32. L. Montagnier et al., in *Human T-cell leukemia/lymphoma virus* (ed. R. C. Gallo et al.), pp. 363–379, Cold Spring Harbor Laboratory, Cold Spring Harbor, N.Y. (1984).
33. M. Popovic et al., *Science* 224, 497 (1984).
34. H. Mitsuya and S. Broder, *Proc. Natl. Acad. Sci. U.S.A.* 83, 1911 (1986).
35. H. Mitsuya and S. Broder, *Nature* 324, 773 (1987).
36. H. Mitsuya et al., *Proc. Natl. Acad. Sci. U.S.A.* 82, 7096 (1985).

What is claimed is:

1. A plasmid identified as pHRTRX2 and deposited in *E. coli* HB101 under ATCC Accession No. 67828.

2. An *E. coli* host cell which comprises the plasmid of claim 1.

3. An *E. coli* HB 101 strain of claim 2, deposited under ATCC Accession No. 67828.

* * * * *